United States Patent
Maev et al.

(10) Patent No.: US 6,297,467 B1
(45) Date of Patent: Oct. 2, 2001

(54) TRANSDUCER BUILT INTO AN ELECTRODE

(75) Inventors: Roman Gr. Maev; Andrei A. Ptchelintsev, both of Windsor; John L. Mann, Amherstburg, all of (CA)

(73) Assignee: DaimlerChrysler Corporation, Auburn Hills, MI (US)

(*) Notice: Subject to any disclaimer, the term of this patent is extended or adjusted under 35 U.S.C. 154(b) by 0 days.

(21) Appl. No.: 09/283,397

(22) Filed: Apr. 1, 1999

(51) Int. Cl.[7] .................................................. B23K 11/25
(52) U.S. Cl. ............................................ 219/109; 219/119
(58) Field of Search .................................. 219/109, 110, 219/119; 73/597, 598

(56) References Cited

U.S. PATENT DOCUMENTS

| | | |
|---|---|---|
| 3,384,733 * | 5/1968 | Burbank et al. ............ 219/109 |
| 3,410,983 * | 11/1968 | Deutsch et al. ............ 219/109 |
| 3,575,044 | 4/1971 | Gibbs et al. . |
| 3,739,628 | 6/1973 | Saglio . |
| 3,868,847 | 3/1975 | Gunkel . |
| 3,895,685 | 7/1975 | Gillette et al. . |
| 3,958,451 | 5/1976 | Richardson . |
| 3,960,005 | 6/1976 | Vezina . |
| 4,012,946 | 3/1977 | Patsey . |
| 4,099,045 * | 7/1978 | Okuda et al. ............ 219/109 |
| 4,208,917 | 6/1980 | Aoyama et al. . |
| 4,449,029 * | 5/1984 | Nied ........................ 219/109 |
| 4,480,475 | 11/1984 | Tsao et al. . |
| 4,711,984 * | 12/1987 | Bilge et al. ............... 219/109 |
| 4,712,722 | 12/1987 | Hood et al. . |
| 4,918,990 * | 4/1990 | Fowler et al. ............. 219/119 |
| 5,060,518 | 10/1991 | Aleshin et al. . |
| 5,439,157 | 8/1995 | Geier et al. . |
| 5,474,225 | 12/1995 | Geier et al. . |
| 5,537,875 | 7/1996 | Viehmann et al. . |
| 5,920,014 * | 7/1999 | Waschkies ................. 73/597 |
| 6,072,144 * | 6/2000 | Perryman ................. 219/109 |

* cited by examiner

Primary Examiner—Clifford C. Shaw
(74) Attorney, Agent, or Firm—Mark P. Calcaterra

(57) ABSTRACT

The present invention provides an electrode assembly for a spot welder which has an acoustic sensor built therein. In a preferred embodiment of the present invention, a spot welder has a first and second electrode assembly according to the present invention. During welding, the acoustic sensor from the first electrode assembly selectively generates a burst of acoustic energy which passes through a weld subject and is received by the second electrode assembly. The acoustic sensor in the second transducer then emits an output signal, representative of the geometry of the weld nugget, to a computer.

10 Claims, 4 Drawing Sheets

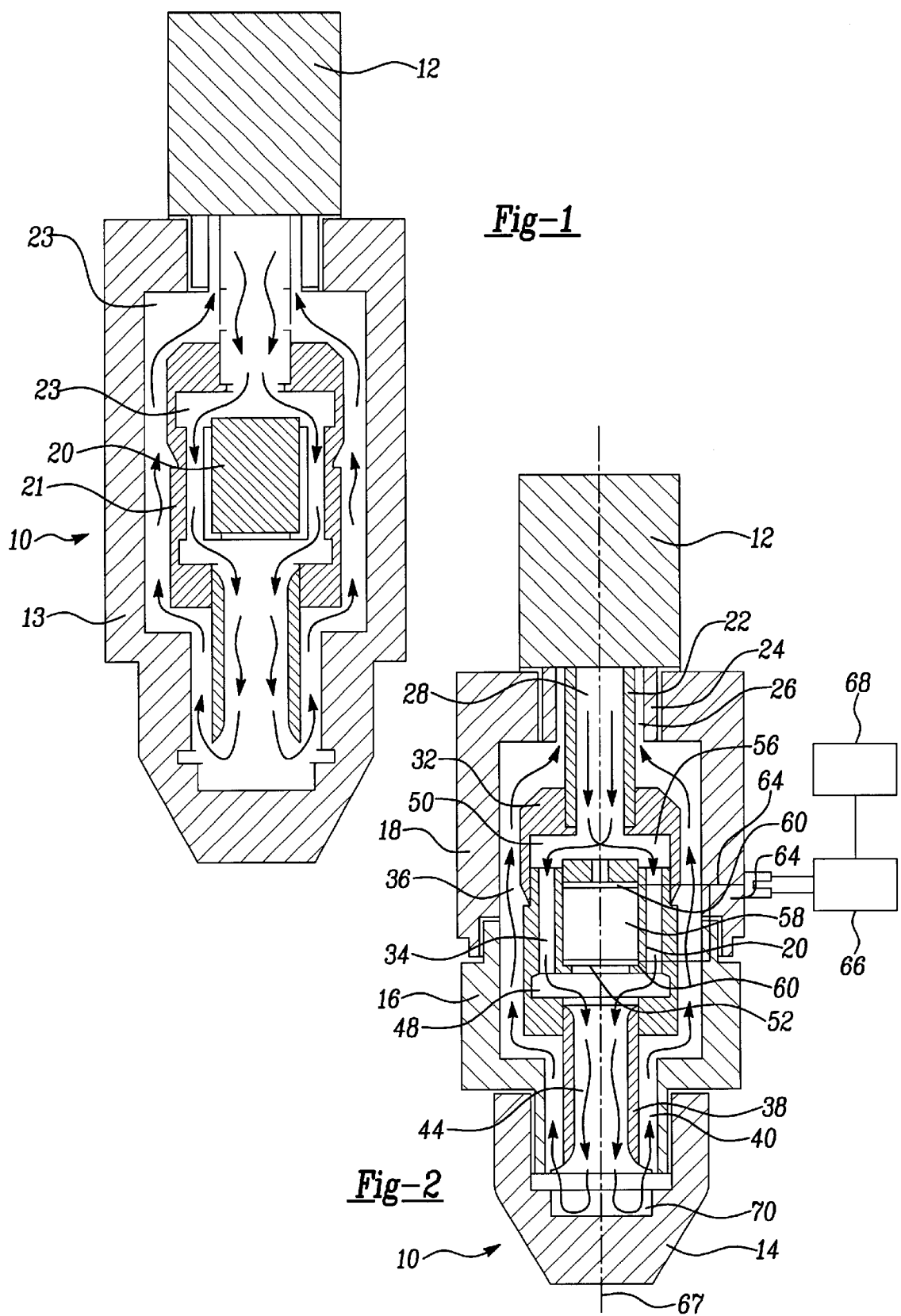

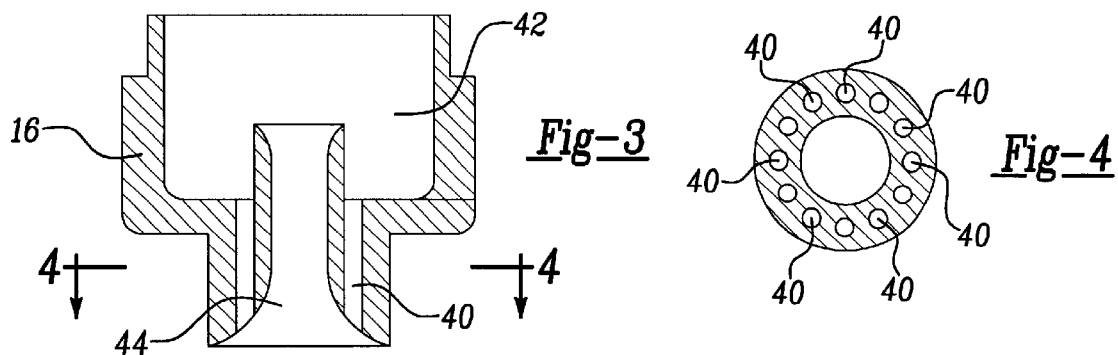
*Fig-3*  *Fig-4*
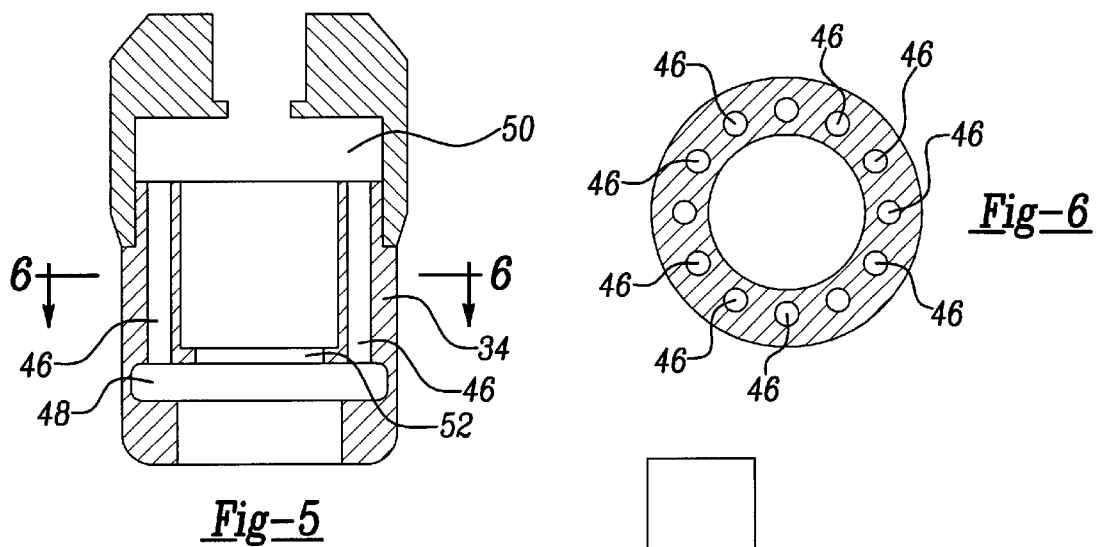
*Fig-5*  *Fig-6*
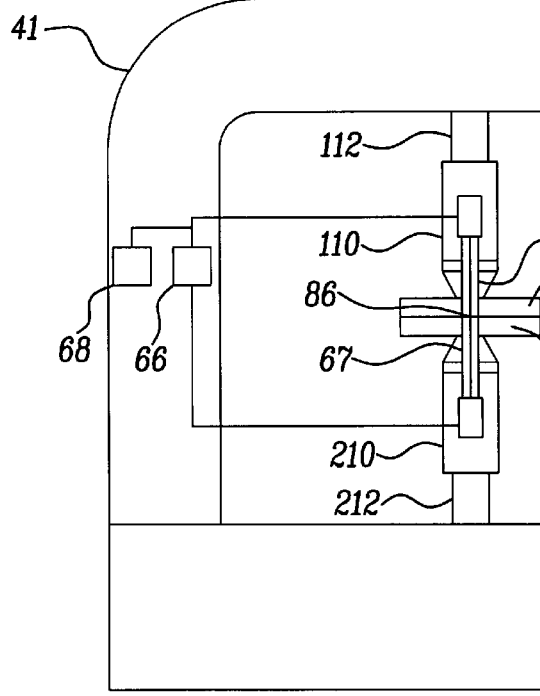
*Fig-7*

TRANSDUCER BUILT INTO AN ELECTRODE

BACKGROUND OF THE INVENTION

Field of the Invention

1. Technical Field

The present invention relates generally to a transducer built into an electrode and, more particularly, to a transducer built into an electrode for real time resistance spot welding monitoring and feedback.

2. Discussion

Welding is a common process for attaching one metal member to another. This process generally involves heating an interface between the items which are to be welded, thereby melting the interface into one joint or weld nugget. Because this process has its application in many different types of manufacturing, such as automobile manufacturing, inspection ensuring that the weld nugget meets certain quality standards is a must. Specifically, it is desirable to inspect the area, size and configuration of the weld nugget and to determine if any defects exist therein. Uninspected welds may result in weld failure after the welded item is sold or distributed to a final user.

Ideally, a weld is inspected either during or shortly after the welding process so that added inspection does not increase weld time, and to allow weld problems to be identified when they occur. Furthermore, non-destructive testing is preferred so that welded parts which pass inspection may still be sold or distributed to the end user.

Visual inspection systems have been employed in the weld environment for this purpose. Specifically, an individual, such as a quality control person, may gage the size of the weld nugget or destructively test a welded item to determine its internal characteristics. However, these methods have several drawbacks. First, because of the bright light and harsh conditions generated by welding, visual inspection of a weld cannot be performed during the welding process. Instead, the welded item must be inspected off line, adding more time and cost to manufacturing. Second, to properly inspect the weld for defects, the internal structure of the weld nugget must be observed. This, in many instances, requires the welded item to be destructively tested, rendering the welded item useless. Besides the increased cost associated with scrapping an item for the purpose of inspection, it is practically impossible to destructively test all items. As such, destructive testing results in a lower number of samples tested and increased cost to manufacturing. The present invention was developed in light of these drawbacks.

SUMMARY OF THE INVENTION

The present invention addresses the aforementioned drawbacks, among others, by providing an electrode assembly for a spot welder which has an ultrasonic probe built therein. In a preferred embodiment of the present invention, a spot welder has a first and second electrode assembly containing first and second ultrasonic probes respectively. During welding, the ultrasonic probe from the first electrode assembly generates a burst of acoustic energy. One portion of this acoustic energy passes through a weld subject and resonates the first ultrasonic probe and another portion is reflected back by the weld subject and is received by the second ultrasonic probe. The ultrasonic probe in the first or second electrode assembly then emits an output signal, representative of the geometry of the weld nugget, to a computer.

Additional advantages and features of the present invention will become apparent from the subsequent description and the appended claims taken in conjunction with the accompanying drawings.

BRIEF DESCRIPTION OF THE DRAWINGS

In the drawings which illustrate the best mode presently contemplated for carrying out the present invention:

FIG. 1 is a cross-sectional view of an electrode assembly according to the present invention;

FIG. 2 is a cross-sectional view of an electrode assembly according to the present invention;

FIG. 3 is a cross-sectional view of a lower adaptor of an electrode assembly according to the present invention;

FIG. 4 is a cross-sectional view of a lower adaptor of an electrode assembly according to the present invention;

FIG. 5 is a cross-sectional view of a lower ultrasonic probe holder of an electrode assembly according to the present invention;

FIG. 6 is a cross-sectional view of a lower ultrasonic probe holder of an electrode assembly according to the present invention;

FIG. 7 is a schematic view of electrode assemblies being used in conjunction with a spot welder according to the present invention;

DETAILED DESCRIPTION OF THE PREFERRED EMBODIMENTS

Figure 8:
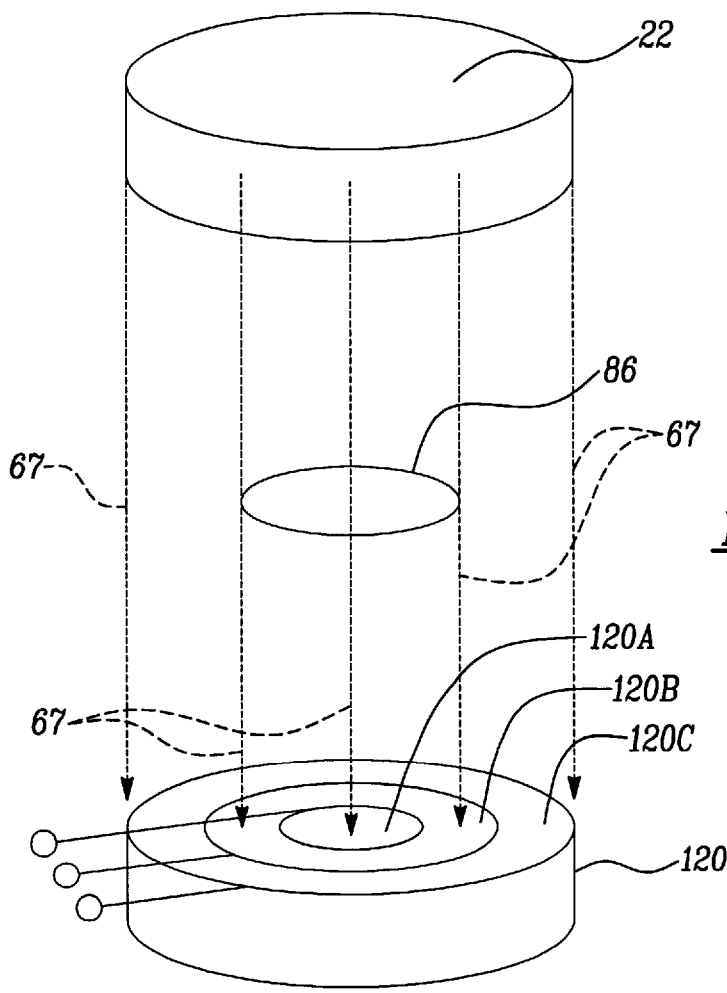
FIG. 8 is a schematic view of ultrasonic probes of electrode assemblies being used according to the present invention.

Referring now to FIG. 1, an electrode assembly 10 according to the present invention is shown attached to an electrode holder 12. As illustrated, electrode assembly 10 generally has four parts, ultrasonic probe 20; structural support system 21; shell 13; and cooling circuit 23, each playing a vital roll in its operation. At its core, electrode assembly 10 has ultrasonic probe 20 which is responsible for generating acoustic energy. Supporting ultrasonic probe 20 within electrode assembly 10 is structural support system 21. This structural support system 21 maintains ultrasonic probe in position while allowing coolant to flow around ultrasonic probe 20 and through electrode assembly 10. The outer periphery of electrode assembly 10 consists of shell 13 which conducts electrical current for spot welding and provides protection to the internal components of electrode assembly 10. Between shell 13 and structural support assembly 21 lies a cooling circuit 23 for cooling shell 13 and ultrasonic probe 20. In the following discussion, each of these elements will be discussed in greater detail.

Referring now to FIG. 2, electrode assembly 10 is shown in greater detail. Here, shell 13 has an has an electrode cap 14, lower adaptor 16 and an upper adaptor 18. To facilitate the flow of coolant from electrode holder 12 to electrode assembly 10, electrode holder 12 is provided with an internal sleeve 22. Sleeve 22 is radially spaced from outer sleeve 24, creating a gap 26 therebetween. This gap 26 allows coolant to flow from electrode assembly 10 and into electrode holder 12. Similar to gap 26, the internal diameter of internal sleeve 22 forms a passage 28 which channels coolant into electrode assembly 10. As such, passage 28 and gap 26 provide the entrance and exit passages for internal cooling circuit 21 within electrode assembly 10.

Internal sleeve 22 and lower adaptor 16 serve as the structural base for structural support system 21 designed to support ultrasonic probe 20. Besides these elements, structural support system 21 generally comprises upper ultrasonic probe holder 32 and lower ultrasonic probe holder 34. Internal sleeve 22, at its lower periphery as shown, attaches to upper ultrasonic probe holder 32. Upper ultrasonic probe holder 32, in turn, attaches to lower ultrasonic probe holder 34. Lower ultrasonic probe holder 34 is then attached to and supported by lower adaptor 16 by sleeve 38. Because only internal sleeve 22 and lower adaptor 16 connect structural support system 21 to shell 13, a gap 36 is formed between structural support system 21 and shell 13. This gap 36 provides a major portion of internal cooling circuit 21 which passage 28 and gap 26 is designed to service.

In FIG. 3, a cross-sectional view of lower adaptor 16 is shown. Channels 40 fluidly connect an upper area 42 with passage 44. In FIG. 4, a cross-sectional view at Section A of FIG. 3 illustrates channels 40 in greater detail. From the illustration, it may be seen that channels 40 generally comprise a plurality of small cylindrical-like tubes. These tubes allow coolant flow through lower adaptor 16 while maintaining its structural integrity.

In FIG. 5, a cross-sectional view of lower ultrasonic probe holder 34 is shown. As illustrated, passages 46 connect upper chamber 50 with lower chamber 48. In FIG. 6 a cross-sectional view at Section B of FIG. 5, similar to lower adaptor 16, shows that passages 46 generally comprise a plurality of cylindrical channels which allow coolant flow and maintain the structural integrity of ultrasonic probe holder 34.

As discussed previously, structural support system 21 provides support for ultrasonic probe 20 and passages for cooling circuit 21. Ultrasonic probe 20 is supported in position by support plate 52, lower ultrasonic probe holder 34, upper ultrasonic probe holder 32, and upper plate 56 as shown. Ultrasonic probe 20, itself, generally comprises piezoelectric crystal 58 sandwiched between conductive plates 60. Conductive plates 60 serve to provide the required current and voltage across piezoelectric crystal 60 to create vibration, thereby inducing a burst of acoustic energy 67. As such, conductive plates 60 are electrically connected to plug 62 by electrical leads 64 to provide the required voltage and current. A power source 66, controlled by computer 68, is connected to plug 62 to provide the required power thereto. During welding, shell 13 provides a conductive path for welding current to be transmitted from electrode holder 12 to a weld subject. As such, electrical current is conducted from electrode holder 12 through upper adaptor 18 and lower adaptor 16, terminating at electrode cap 14. The electrode cap 14, itself, is the element which is in contact with items which are to be welded.

To cool the electrode assembly 10 and protect the ultrasonic probe 20, cooling circuit 23 is provided. In cooling circuit 21, coolant is transmitted from electrode holder 12 through internal portion 28 and into upper chamber 50. Coolant moves from upper chamber 50, through passages 46 of lower ultrasonic probe holder 34 and into lower chamber 48, thereby ensuring that ultrasonic probe 20 remains cool. Coolant then passes from lower chamber 48, through passage 44 of lower adaptor 16, to area 70 within electrode cap 14, thereby cooling electrode cap 14. Coolant next moves from area 70 into channels 40 of lower adaptor 16, through gap 36, thereby cooling lower adaptor 16 and upper adaptor 18, and exits through gap 26.

Referring now to FIG. 7, the operation of the present invention will now be described. In FIG. 7, upper electrode assembly 110 and lower electrode assembly 210, having the same components as electrode assembly 10, are shown attached to upper electrode holder 112 and lower electrode holder 212, respectively. Upper electrode holder 112 and lower electrode holder 212 are mechanically and electrically engaged with spot welder 41 as is known.

During operation, weld subject 80, here consisting of two or more overlapping plates 84 and 86, are clamped between lower electrode assembly 210 and upper electrode assembly 110. Electrical current is then transmitted from upper electrode assembly 110 to lower electrode assembly 210, through weld subject 80, creating weld nugget 86.

When weld subject 80 is initially clamped and before weld current flow and formation of weld nugget 86, computer 68 instructs upper electrode assembly 110 to generate bursts of acoustic energy 67 which pass through and are reflected by upper plate 82, weld nugget 86, and lower plate 84. These bursts continue until after weld nugget 86 has been formed and cooled. The portion of each Burst of acoustic energy 67 which passes through these elements, intersects and resonates piezoelectric crystal 58 of lower electrode assembly 210. The portion which is reflected by these elements, resonates piezoelectric crystal 58 of upper electrode assembly 110. This resonation induces a current in conductive plates 60, sending electrical signals to computer 68.

Figure 10:
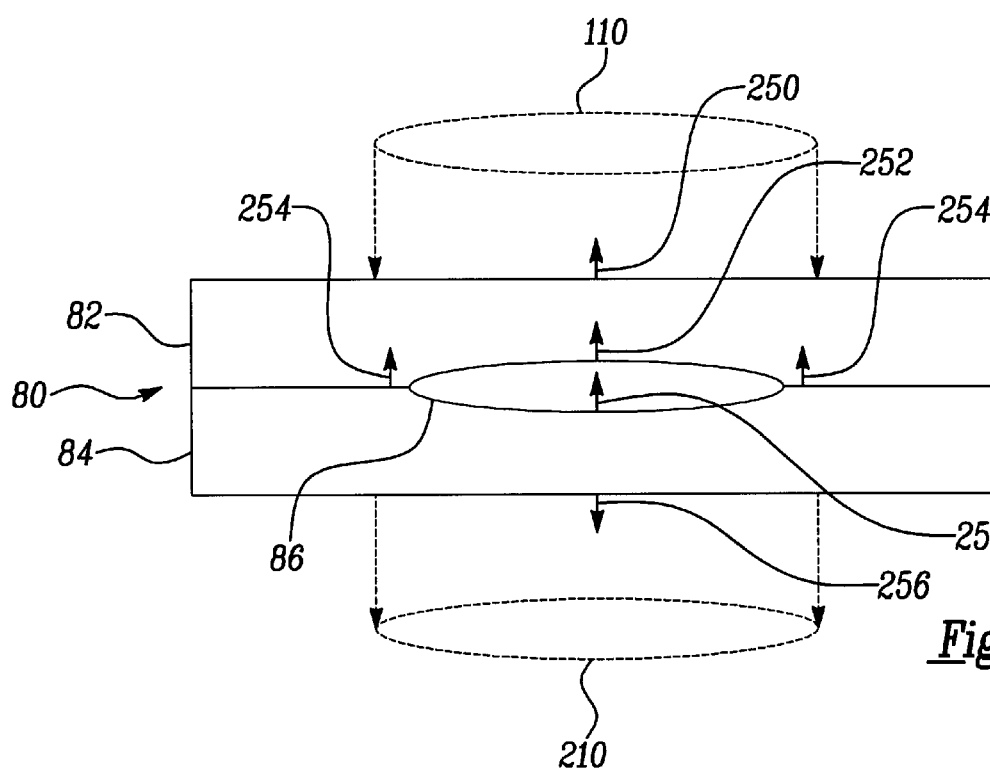
FIG. 10 is a schematic view of ultrasonic probes of electrode assemblies being used according to the present invention.

Referring now to FIG. 10, a schematic illustrating weld subject 80, upper electrode assembly 110 and lower electrode assembly 210 is provided. Rays 250, 252, 254, and 258 are reflected portions of initial burst of acoustic energy 67. Different portions of burst of acoustic energy 67 reflect off different portions of weld subject 80. Specifically, ray 250 represents acoustic energy reflected upward from the upper surface of upper weld plate 82, ray 252 represents acoustic energy reflected from upper portion of weld nugget 86, rays 254 represent acoustic energy reflected from the interface between upper plate 82 and lower plate 84, and ray 258 represents acoustic energy reflected from the interface between weld nugget 86 and lower plate 84. Similarly, ray 256 represents acoustic energy which passes through weld subject 80 and ultimately intersects and resonates piezoelectric crystal 58 of lower electrode assembly 210.

The time of flight (TOF), time from transmission of burst of acoustic energy 67 until reception, is indicative of certain characteristics of weld subject 80, weld nugget 86 and even upper electrode 110.

Figure 11:
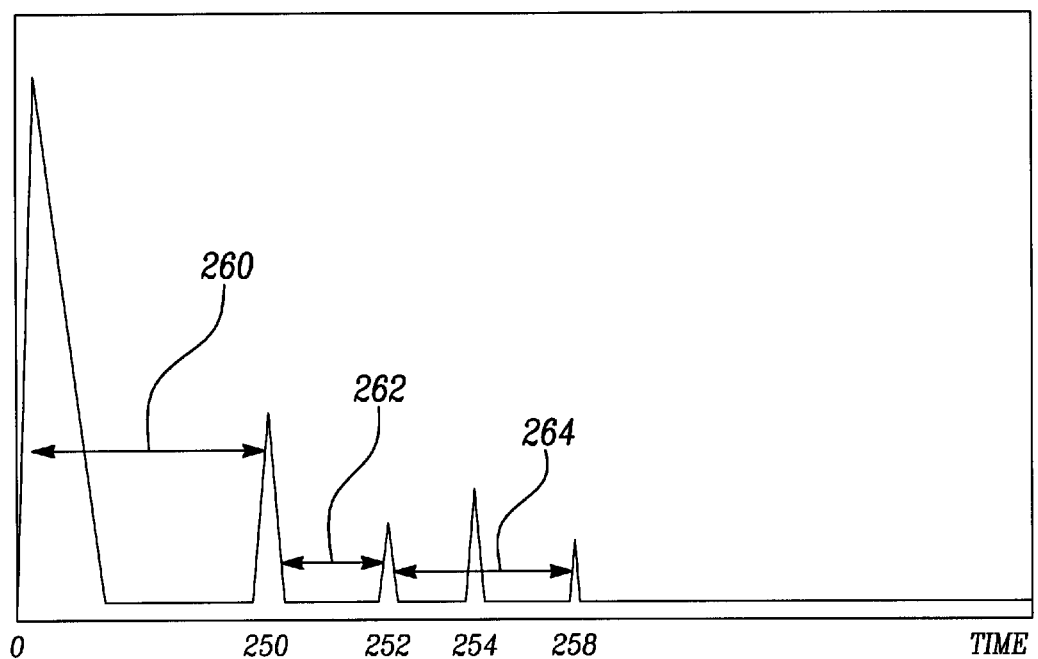
FIG. 11 is a graphical representation of operating characteristics according to the present invention.

Referring now to FIG. 11, a time amplitude graph is shown which plots each ray 250, 252, 254 or 258 in time. Each spike represents the signal strength, generated by resonation of piezoelectric crystal 58 in upper electrode assembly 110. The time between each of these spikes is used to determine certain characteristics about weld subject 80 and upper electrode assembly 110. For instance, the TOF of ray 250 (TOF 260 in FIG. 11), which represents time between transmission and reception of acoustic energy which results in ray 250, can be used to determine the wear of upper electrode assembly 110. Likewise, ray 252 together with ray 250 can be used to generate TOF 262 used to determine the residual thickness of upper plate 82, and together with ray 258 can be used to generate TOF 264 and determine the thickness of weld nugget 86. Rays 254, which are reflected only outside weld nugget 86, can be used to determine the cross section of weld nugget 86.

Ray 256 is used by computer 68 generate a time history of the welding process. This time history follows a somewhat predictable pattern from which characteristics of the weld nugget 86 may be configured. Initially, when plates 84 and 86 are clamped between lower electrode assembly 210 and upper electrode assembly 110, before the flow of electrical current begins and before maximum clamping pressure, the strength of ray 256 is small and the electrical signal generated from lower electrode assembly 210, in response to ray 256, is near zero. As the applied force from the clamping action of upper electrode assembly 110 and lower electrode assembly 210 increases, the strength of ray 256 increases to a peak, then remains constant until the welding current is generated. During heating, the strength of ray 256 increases causing the signal produced by piezoelectric crystal 58 to likewise increase. After current flow and during cooling of weld nugget 86, the signal strength fluctuates according to temperature and phase transition of the cooling metal.

This signal strength and fluctuation during the welding process can be used to form a kind of acoustic signature of the process and determine certain characteristics of the weld nugget 86. In particular, primary informative parameters of the signal (magnitude and phase) tend to follow the metal heating and melting stages. Experimental ultrasonic patterns, as a function of time, as well as real time welding current values, tend to correlate with the diameter of the weld nugget 86. By using a representative set of the signatures and comparing them with destructive tests (peel tests), quantitative calibration characteristics can be established. Those calibration characteristics can be explicit ones, or the final guess about the weld could be established using neural networking algorithms. Either way, this information can be used to determine valuable information about the weld subject 80.

Figure 9:
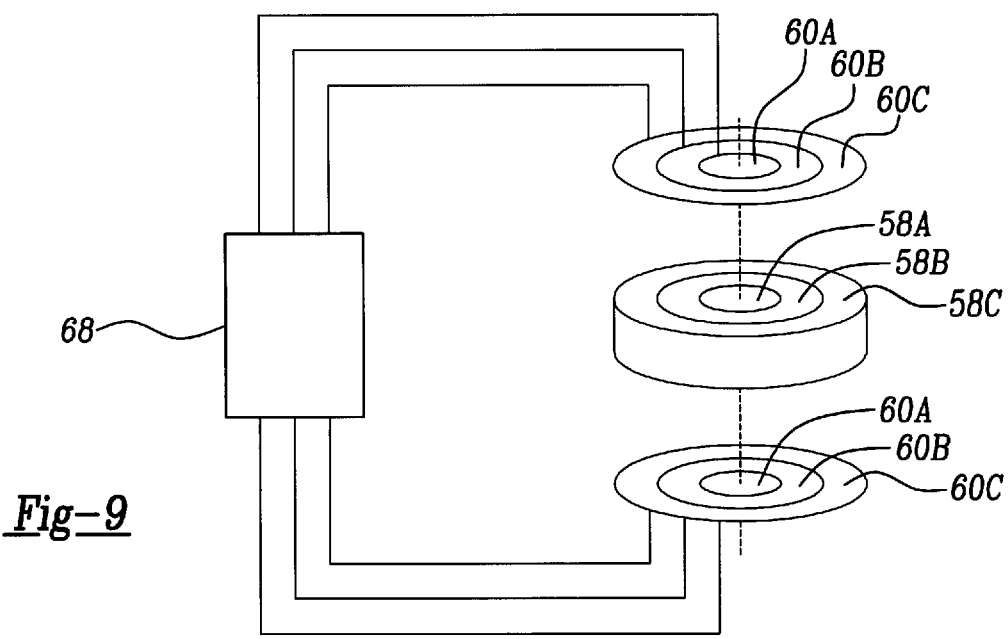
FIG. 9 is an exploded view of an ultrasonic probe according to the present invention.

Referring now to FIGS. 8 and 9, ultrasonic probe 20 of lower electrode assembly 210 is replaced with ultrasonic array 120. Ultrasonic array 120 differs from ultrasonic probe 20 in that ultrasonic array 120 has a plurality of sensing elements as opposed to only one. In FIG. 8, ultrasonic array 120 is shown having a plurality of independent ultrasonic probes 120A, 120B, and 120C, each generating an output signal independent from the remainder. To form these elements, each independent piezoelectric crystal 58A, 58B, and 58C is sandwiched by independent conductive plates 60A, 60B, and 60C. Each set of conductive plates 60A, 60B, and 60C communicates with computer 68, allowing each independent piezoelectric crystal 58A, 58B, and 58C to provide a different output signal to computer 68.

In operation, each burst of acoustic energy 67 intersects various and different portions of ultrasonic array 120. As such, bursts of acoustic energy 67 which pass through weld nugget 86 may intersect one portion of ultrasonic array 120 while other bursts of acoustic energy 67 intersect other portions of ultrasonic array 120. For example, as shown in FIG. 7, bursts of acoustic energy 67 which pass through weld nugget 86 intersect independent piezoelectric crystal 58A while bursts of acoustic energy 67 which bypass weld nugget 86 intersect independent piezoelectric crystals 58B and 58C. As such, the outputs generated by independent piezoelectric crystal 58A will be different than the outputs from independent piezoelectric crystals 58B and 58C. The result is that computer 68 is able to analyze the received information and provide a more accurate result of the size and geometry of weld nugget 86. It is noted that ultrasonic probe 20 of upper electrode assembly 110 may be also constructed similar to ultrasonic array 120, thereby providing a plurality of independent and separate bursts of acoustic energy 67.

While the above detailed description describes the preferred embodiment of the present invention, it should be understood that the present invention is susceptible to modification, variation, and alteration without deviating from the scope and fair meaning of the subadjoined claims.

What is claimed is:

1. A spot welder comprising:
   a first electrode assembly and a second electrode assembly, each of said electrode assemblies selectively conducting a weld current through a weld subject for spot welding, each of said electrode assemblies having an ultrasonic probe, said ultrasonic probes at least partially surrounded by an outer shell; and
   said ultrasonic probe of said first electrode assembly selectively generating a burst of acoustic energy through a weld subject, wherein each of said ultrasonic probes receives a portion of said burst of acoustic energy for providing at least one output signal representative of measurements of a weld nugget of said weld subject.

2. A spot welder as claimed in claim 1, further comprising a computer receiving said output signal and providing a visual display representative of said measurements of said weld nugget.

3. A spot welder as claimed in claim 1, wherein said measurements are a member of the set consisting of width, volume and temperature.

4. A spot welder as claimed in claim 1, wherein said ultrasonic sensor of said second electrode assembly is an ultrasonic array.

5. A spot welder as claimed in claim 1, wherein said first electrode assembly and said second electrode assembly each have an output plug to provide electrical communication with said first ultrasonic sensor and said second ultrasonic sensor.

6. A method for monitoring a welding process of a weld subject, comprising the steps of:
   a. clamping a weld subject between a first electrode and a second electrode;
   b. transmitting a series of bursts of acoustic energy from a first ultrasonic probe disposed within said first electrode and receiving portions of said bursts of acoustic energy with said first ultrasonic probe and a second ultrasonic probe disposed within said second electrode, said series of bursts of acoustic energy being transmitted until after welding is complete;
   c. welding said weld subject; and
   d. generating a first output signal from said first ultrasonic probe and a second signal from said second ultrasonic probe which are representative of measurements of said weld subject.

7. The method as claimed in claim 6, wherein said first ultrasonic probe and said second ultrasonic probe are located within said first electrode and said second electrode respectively.

8. The method as claimed in claim 6, further comprising a computer which determines a time of flight of said bursts of acoustic energy, said computer determining said measurements of a weld nugget contained within said weld subject from said time of flight of said bursts of acoustic energy.

9. The method as claimed in claim 6, wherein said measurements of said weld nugget are width and location.

10. The method as claimed in claim 6, wherein said second output signal represents a time history of said welding process.

* * * * *